(12) United States Patent
Zhang et al.

(10) Patent No.: US 12,266,105 B2
(45) Date of Patent: Apr. 1, 2025

(54) BONE STRENGTH SIMULATION CALCULATION METHOD AND DEVICE, AND STORAGE MEDIUM

(71) Applicant: THE FIRST MEDICAL CENTER OF PLA GENERAL HOSPITAL, Beijing (CN)

(72) Inventors: Lihai Zhang, Beijing (CN); Shuwei Zhang, Beijing (CN); Tie Wang, Tianjin (CN); Lei Hu, Beijing (CN); Ying Hu, Guangdong (CN)

(73) Assignee: THE FIRST MEDICAL CENTER OF PLA GENERAL HOSPITAL, Beijing (CN)

( * ) Notice: Subject to any disclaimer, the term of this patent is extended or adjusted under 35 U.S.C. 154(b) by 0 days.

(21) Appl. No.: 18/432,357

(22) Filed: Feb. 5, 2024

(65) Prior Publication Data

US 2024/0177303 A1 May 30, 2024

Related U.S. Application Data

(63) Continuation of application No. PCT/CN2021/142019, filed on Dec. 28, 2021.

(30) Foreign Application Priority Data

Aug. 6, 2021 (CN) .......................... 202110901045.6

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/032* (2013.01); *A61B 6/505* (2013.01); *G06T 7/11* (2017.01);
(Continued)

(58) Field of Classification Search
CPC ......... G06T 7/0012; G06T 7/11; G06T 7/149; G06T 7/187; G06T 7/60; G06T 7/75;
(Continued)

(56) References Cited

U.S. PATENT DOCUMENTS

2006/0069318 A1* 3/2006 Keaveny .................. G06T 7/97
703/11
2009/0177282 A1* 7/2009 Bureau ................. B29C 70/025
264/134
(Continued)

FOREIGN PATENT DOCUMENTS

CN 106548515 A 3/2017
CN 110363765 A 10/2019
(Continued)

OTHER PUBLICATIONS

International Search Report of PCT Patent Application No. PCT/CN2021/142019 issued on Apr. 26, 2022.
(Continued)

*Primary Examiner* — Hien N Nguyen

(57) ABSTRACT

A bone strength simulation calculation method and device, and a storage medium. The bone strength simulation calculation method includes acquiring three-dimensional data of cancellous bone of a bone segment to be analyzed; obtaining a skeleton mechanical model according to the three-dimensional data; and performing feature analysis on the skeleton mechanical model to obtain skeleton strength data.

10 Claims, 4 Drawing Sheets

(51) Int. Cl.
*A61B 6/50* (2024.01)
*G06T 7/11* (2017.01)
*G06T 7/149* (2017.01)
*G06T 7/187* (2017.01)
*G06T 7/60* (2017.01)
*G06T 7/73* (2017.01)
*G06T 11/00* (2006.01)
*G06T 19/00* (2011.01)

(52) U.S. Cl.
CPC .............. *G06T 7/149* (2017.01); *G06T 7/187* (2017.01); *G06T 7/60* (2013.01); *G06T 7/75* (2017.01); *G06T 11/008* (2013.01); *G06T 19/00* (2013.01); *G06T 2200/04* (2013.01); *G06T 2207/10081* (2013.01); *G06T 2207/20081* (2013.01); *G06T 2207/20156* (2013.01); *G06T 2207/30008* (2013.01); *G06T 2207/30204* (2013.01); *G06T 2210/41* (2013.01); *G06T 2211/441* (2023.08)

(58) Field of Classification Search
CPC ... G06T 11/008; G06T 19/00; G06T 2200/04; G06T 2207/10081; G06T 2207/20081; G06T 2207/20156; G06T 2207/30008; G06T 2207/30204; G06T 2210/41; G06T 2211/441; A61B 6/032; A61B 6/505
See application file for complete search history.

(56) References Cited

U.S. PATENT DOCUMENTS

| | | | |
|---|---|---|---|
| 2016/0157936 A1 | 6/2016 | Netravali | |
| 2018/0116584 A1* | 5/2018 | Kopperdahl | A61B 5/4509 |
| 2018/0247020 A1* | 8/2018 | Itu | G16H 10/60 |
| 2019/0183410 A1* | 6/2019 | Rajapakse | A61B 5/4504 |
| 2020/0275880 A1* | 9/2020 | Kopperdahl | G16H 50/30 |

FOREIGN PATENT DOCUMENTS

| | | |
|---|---|---|
| CN | 112529863 A | 3/2021 |
| CN | 113658706 A | 11/2021 |

OTHER PUBLICATIONS

Written Opinion of the International Searching Authority of PCT Patent Application No. PCT/CN2021/142019 issued on Apr. 26, 2022.

\* cited by examiner

BONE STRENGTH SIMULATION CALCULATION METHOD AND DEVICE, AND STORAGE MEDIUM

CROSS REFERENCE TO RELATED APPLICATION

The present application is a Continuation Application of PCT Application No. PCT/CN2021/142019 filed on Dec. 28, 2021, which claims the benefit of Chinese Patent Application No. 202110901045.6 filed on Aug. 6, 2021. All the above are hereby incorporated by reference in their entirety.

TECHNICAL FIELD

The disclosure relates to the technical field of bone strength assessment, in particular to a bone strength simulation calculation method, device and storage medium.

BACKGROUND

There are many methods for measuring bone mineral content, and the most widely used methods are quantitative computed tomography (QCT) and dual energy X-ray absorptiometry (DXA). The DXA can reflect the sum of cortical bone and cancellous bone, and the measurement result is area bone density in g/cm2. The method of QCT is to use conventional CT plus phantom, scan the lumbar spine and the reference phantom below the lumbar spine simultaneously, and then define the region of interest (ROI) as the trabecular bone in the cancellous bone of the middle layer of each vertebral body on the CT image, and obtain the bone density value of the cancellous bone of each vertebral body through computer processing and analysis, and then further calculate the average value of the measured lumbar bone density, which can separate the cortical bone from the cancellous bone and measure the real cancellous bone density. The measurement result is the volume bone density in g/cm3.

SUMMARY

One aspect of the present disclosure provides a bone strength simulation calculation method, including:
  obtaining three-dimensional data of a cancellous bone of the bone segment to be analyzed;
  obtaining a skeleton mechanical model according to the three-dimensional data;
  performing a feature analysis on the skeleton mechanical model to obtain skeleton strength data.

Further, the obtaining three-dimensional data of a cancellous bone of the bone segment to be analyzed, includes:
  obtaining the three-dimensional data of the cancellous bone of the bone segment to be analyzed by using a Quantitative Computed Tomography, QCT measurement method.

Further, the obtaining a skeleton mechanical model according to the three-dimensional data, includes:
  performing a three-dimensional reconstruction according to the three-dimensional data to obtain a spatial structure of a trabecular bone;
  skeletonizing obtained spatial structure of the trabecular bone to obtain a mechanical model of the trabecular bone, wherein the mechanical model of the trabecular bone is the skeleton mechanical model.

Further, trabeculae in the cancellous bone are interwoven with each other, and joints of three or more trabeculae are trabecular nodes;
  the skeleton strength data includes a quantity data of the trabecular nodes, and/or data of angle between trabecular bones of the trabecular nodes.

Further, the performing a feature analysis on the skeleton mechanical model to obtain skeleton strength data, includes:
  determining a quantity of bone trabeculae constituting each trabecular node in the skeleton mechanical model to obtain a type of each trabecular node;
  extracting a quantity data of discriminant trabecular nodes in various types of trabecular nodes.

Further, the discriminative trabecular nodes include trifurcated nodes, quad nodes, and pentagonal nodes.

Further, the performing a feature analysis on the skeleton mechanical model to obtain skeleton strength data, includes:
  extracting at least one type of trabecular node as a pedestal trabecular node;
  determining angles between each bone trabeculae constituting the pedestal trabecular node successively to obtain data of angles between each pedestal trabecular node.

Further, the performing a feature analysis on the skeleton mechanical model to obtain skeleton strength data, further includes:
  performing a finite element simulation on the angles between the trabecular bones of the pedestal trabecular nodes to obtain a maximum stress of each angle type.

Further, the extracting at least one type of trabecular node as a pedestal trabecular node, includes:
  extracting a type of trabecular node with a largest quantity from various types of trabecular nodes as the pedestal trabecular node.

Further, the pedestal trabecular node includes trifurcated nodes.

Further, the determining a quantity of bone trabeculae constituting each trabecular node in the skeleton mechanical model, includes:
  marking each pixel of the skeleton mechanical model according to an order of length*width*height l*m*n, wherein a range of mark value is 0 to l*m*n−1;
  extracting pixels whose dark-and-bright indication values meet a preset skeleton threshold in an image of the skeleton mechanical model, marking the pixels as skeleton points;
  traversing the skeleton points of the skeleton mechanical model with a three-dimensional voxel model, extracting with more than three skeleton points at neighboring point positions, and marking the pixel points as candidate nodes;
  pushing coordinates of the candidate nodes into a stack as a seed point for region growth, and setting a tag value of the candidate nodes as a tag value of the candidate nodes;
  performing a neighborhood search on the candidate nodes in the stack successively to determine whether the tag value of the candidate nodes is modified, and if not, popping the candidate nodes out of the stack until a distance between a spread candidate node and a first candidate node is greater than a preset search radius or there is no such spread candidate node;
  removing a candidate node whose distance from the candidate nodes in the stack is less than a preset minimum distance threshold, counting a quantity and coordinates of remaining candidate nodes, and determining a quantity of trabecular bone forming the trabecular node according to the quantity of the remaining candidate nodes.

Further, the performing a feature analysis on the skeleton mechanical model to obtain the skeleton strength data, comprises, applying a first bone strength value calculation formula to obtain the skeleton strength data:

$$E1 = e\sigma_{yield} + fK + gM,$$

wherein E1 is the first bone strength value, e, f, and g are coefficients, $\sigma_{yield}$ is the maximum stress of the pedestal trabecular nodes, K is a weight of proportion of the discriminative trabecular nodes, and M is a weight of proportions of various angle modes in the pedestal trabecular nodes.

Further, the bone strength simulation calculation method further includes: applying a machine learning method to train the first bone strength value calculation formula.

Further, in response to the machine learning method being applied to train the first bone strength value calculation formula, obtaining training samples, includes:

performing an image scanning on a training bone segment, performing a geometric feature calculation and a finite element analysis on an obtained image of the training bone segment, and conducting mechanical experiments on the training bone segment;

obtaining a first bone strength marker value according to a calculation result of geometric features, a result of finite element analysis and results of mechanical experiments;

marking the training bone segment and the first bone strength marker value of the training bone segment as the training samples.

Further, the bone strength simulation calculation method further includes:

obtaining bone density data of the cancellous bone of the bone segment to be analyzed;

obtaining comprehensive bone strength data according to the skeleton strength data and the bone density data.

Further, the obtaining comprehensive bone strength data according to the skeleton strength data and the bone density data, includes: applying a following comprehensive bone strength value calculation formula to obtain the comprehensive bone strength data:

$$E = aT + b\sigma_{yield} + cK + dM;$$

wherein E is the comprehensive bone strength value, a, b, c, d are coefficients, T is the bone density data, $\sigma_{yield}$ is a maximum stress of the pedestal trabecular nodes, and K is a weight of proportion of the discriminative trabecular node, M is a weight of the proportions of different angle modes in the pedestal trabecular nodes.

Further, the bone strength simulation calculation method further includes: applying a machine learning method to train the comprehensive bone strength value calculation formula.

Further, in response to the machine learning method being applied to train the comprehensive bone strength value calculation formula, obtaining training samples, comprises:

performing an image scanning on a training bone segment, performing a geometric feature calculation and a finite element analysis on an obtained image of the training bone segment, and conducting mechanical experiments on the training bone segment;

obtaining a comprehensive bone strength marker value according to a bone density calculation result, a calculation result of geometric features, a result of finite element analysis and results of mechanical experiments;

marking the training bone segment and the comprehensive bone strength marker value of the training bone segment as the training samples.

Another aspect of the present disclosure provides a bone strength simulation calculation device, including a processor and a memory, wherein the memory is configured to store computer instructions, and the processor is configured to execute the computer instructions stored in the memory, in response to the computer instructions are executed by the processor, the device implements any one of above method.

Yet another aspect of the present disclosure provides a computer storage medium, storing a computer program, wherein in response to the computer program being executed by a processor, any one of above method is implemented.

BRIEF DESCRIPTION OF FIGURES

In order to more clearly illustrate the specific implementation of the present disclosure or the technical solutions in the prior art, the following will briefly introduce the accompanying drawings that need to be used in the specific implementation or description of the prior art. Obviously, the accompanying drawings in the following description show some implementations of the present disclosure, and those skilled in the art can obtain other drawings based on these drawings without any creative work.

DETAILED DESCRIPTION

Figure 1:
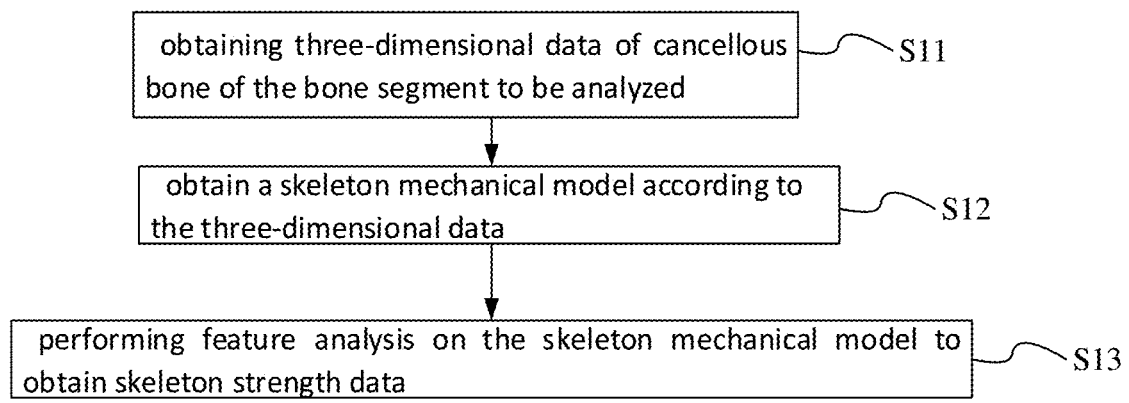
FIG. 1 is the flowchart of the method for assessing bone strength described in Embodiment 1 of the present disclosure.

The technical solutions of the present disclosure will be clearly and completely described below in conjunction with the accompanying drawings. Apparently, the described embodiments are some of the embodiments of the present disclosure, but not all of them. Based on the embodiments of the present disclosure, all other embodiments obtained by persons of ordinary skill in the art without making creative efforts belong to the protection scope of the present disclosure.

In the description of the present disclosure, it should be noted that the terms "center", "upper", "lower", "left", "right", "vertical", "horizontal", "inner", "outer" etc., indicated orientation or positional relationship is based on the orientation or positional relationship shown in the drawings, and is only for the convenience of describing the present disclosure and simplifying the description, rather than indicating or implying that the referred device or element must have a specific orientation, or construction and operation in a specific orientation, therefore, it should not be construed as limiting the disclosure. In addition, the terms "first", "second", and "third" are used for descriptive purposes only, and should not be construed as indicating or implying relative importance.

In the description of the present disclosure, it should be noted that unless otherwise specified and limited, the terms "installation", "connection" and "link" should be understood in a broad sense, for example, it can be a fixed connection or a detachable connection, or integrally connected; it may be mechanically connected or electrically connected; it may be directly connected or indirectly connected through an intermediary, and it may be the internal communication of two components. Those of ordinary skill in the art can understand the specific meanings of the above terms in the present disclosure in specific situations.

Prior evaluations of bone strength are roughly based on bone density values, and all of them have defects. The DXA is a two-dimensional bone density measurement, which reflects the area density rather than the real volume, that is, the bone density measured by the DXA is the sum of all the bones in the scanning area, and the cortical bone and cancellous bone cannot be distinguished. The cortical bone will reduce the sensitivity of observing treatment changes, and the bone density measured by the DXA is obviously affected by the geometric shape, so even if the actual bone density is the same, if the DXA is used, the density of thick bone is higher than the density of thin bone. The density of spine measured by the DXA includes the area density of the entire vertebral body including the vertebral body and the vertebral arch. Aortic calcification, degenerative osteoarthrosis, bone hyperplasia, spinous processes, calluses, and compression fractures can all lead to increased bone density. The QCT can obtain the bone density value of the cancellous bone of each vertebral body, and further calculate the average value of the measured lumbar bone density in g/cm3, which is a simple density value, although it can solve some problems of the DXA, but the density value can only roughly evaluate the bone strength, and cannot fully reflect the bone strength.

Therefore, in view of the above problems, the present disclosure urgently needs to provide a new bone strength simulation calculation method, device and storage medium.

Embodiment 1

Figure 2:
FIG. 2 is a schematic diagram of the spatial structure of the trabecular bone described in Embodiment 1 of the present disclosure.
Figure 3:
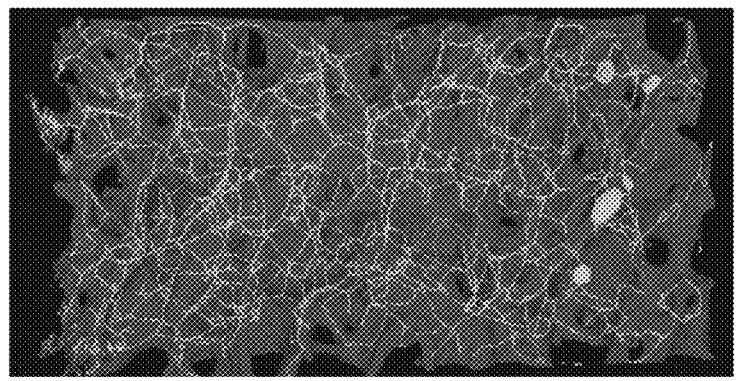
FIG. 3 is a schematic structural view of the skeleton mechanical model described in Embodiment 1 of the present disclosure.

As shown in FIG. 1, FIG. 2, and FIG. 3, a calculation method for bone strength simulation provided in this embodiment includes the following steps:
S11. obtaining three-dimensional data of cancellous bone of the bone segment to be analyzed;
S12. obtain a skeleton mechanical model according to the three-dimensional data;
S13. performing feature analysis on the skeleton mechanical model to obtain skeleton strength data.

The calculation method for bone strength simulation provided by the present disclosure obtains the skeleton mechanical model based on reconstruction of the three-dimensional data, and then performs feature analysis on the skeleton mechanical model to obtain the skeleton strength data, which is used to assist in judging strength design of the bone segment to be analyzed, performs a simulated reconstruction of the data of the bone segment to be analyzed, and then performs the feature analysis on the reconstructed skeleton mechanical model. According to the theory of Young's modulus of elasticity, the greater the strength is, the smaller the elasticity is, the strength of the skeleton structure can be effectively obtained, so as to provide strong evidence for the subsequent judgment of bone strength and increase the accuracy and reliability of bone strength assessment results.

In the present disclosure, the specific process of obtaining the three-dimensional data of the cancellous bone of the bone segment to be analyzed can be directly extracting the three-dimensional data of the cancellous bone from the stored medical image data, or can be obtaining the three-dimensional data of the cancellous bone through detecting the bone segment to be analyzed using any existing detection means of the three-dimensional data of the cancellous bone, and those skilled in the art can obtain the current method according to the actual needs. Of course, in order to obtain more accurate three-dimensional data of the cancellous bone of the bone segment to be analyzed, the obtaining the three-dimensional data of the cancellous bone of the bone segment to be analyzed, specifically includes:
obtaining the three-dimensional data of cancellous bone in the bone segment to be analyzed by using the QCT measurement method.

Referring to FIG. 2 and FIG. 3, in the present embodiment, the obtaining skeleton mechanical model according to the three-dimensional data, specifically include:
performing three-dimensional reconstruction according to the three-dimensional data to obtain the spatial structure of the trabecular bone;
skeletonizing the obtained spatial structure of the trabecular bone to obtain a mechanical model of the trabecular bone, that is, the skeleton mechanical model.

The present disclosure obtains a skeleton mechanical model based on the three-dimensional data, which specifically includes: performing three-dimensional reconstruction according to the three-dimensional data to obtain the spatial structure of the trabecular bone; performing skeletonization processing on the obtained spatial structure of the trabecular bone to obtain a mechanical model of bone trabecular, that is, the design of the skeleton mechanical model. The skeletonized mechanical model shows a more concise skeleton structure, which eliminates the influence of factors such as bone trabecular thickness on the structural strength; at the same time, it reduces the amount of calculation and reduces the calculation time of the skeleton strength data and the requirements for the computer hardware system when the method is applied, without affecting the skeleton strength data as much as possible.

Figure 4:
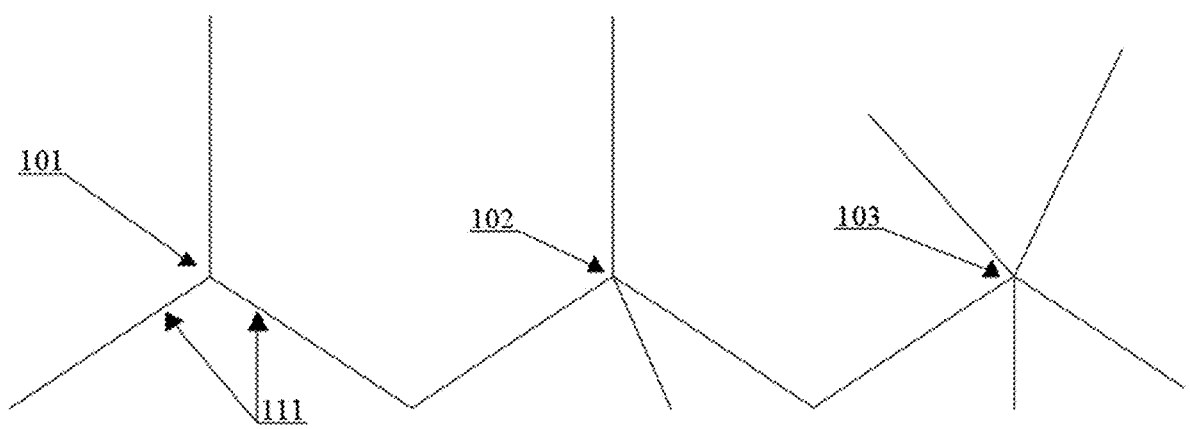
FIG. 4 is a schematic structural view of the trabecular nodes described in Embodiment 1 of the present disclosure.

Referring to FIG. 4, in this embodiment, the trabecular bones 111 in the cancellous bone interweaves with each other, and a joint of three or more trabecular bones is a trabecular node.

The skeleton strength data includes the quantity data of trabecular nodes, and/or the data of the angle between trabecular bones of the trabecular nodes.

The present disclosure adopts the skeleton strength data including the quantity data of trabecular nodes and/or, the design of data of the angle between the trabecular bone of the trabecular nodes, and extracts the quantity and the angle between trabecular bones of trabecular nodes which make the greatest influence on the bone strength as the skeleton strength data, which has the characteristics of high correlation with bone strength and makes the evaluation results accurate. The quantity data of trabecular nodes or the angle between trabecular bones of trabecular nodes are the main structural factors that affect the skeleton strength. The more types of skeleton strength data are selected, the more comprehensive the bone strength evaluation will be. Certainly, the more skeleton strength data are selected, the greater the calculation amount is, and those skilled in the art can select the types included in the skeleton strength data according to actual needs.

Referring to FIG. 4, in the present embodiment, the performing the feature analysis on the skeleton mechanics model to obtain the skeleton strength data, includes:
  determining the quantity of bone trabeculae forming each trabecular node in the skeleton mechanics model to obtain the type of each trabecular node;
  extracting the quantity data of discriminative trabecular nodes among various types of trabecular nodes.

The determining the quantity of trabecular bones forming each trabecular node in the skeleton mechanical model to obtain the type of each trabecular node is: successively determining the quantity of trabecular bones of each trabecular node in the skeleton mechanical model. Of course, the type of trabecular nodes is determined according to the quantity of bone trabeculae that form the trabecular nodes. There are usually trifurcated nodes 101, quad nodes 102, pentagonal nodes 103, hexagonal nodes and other types in the cancellous bone.

In this embodiment, the determined types of trabecular nodes include trifurcated nodes, quad nodes and pentagonal nodes.

In this embodiment, the performing feature analysis on the skeletal mechanical model subjected to obtain skeletal strength data, includes:
  extracting at least one type of trabecular node as the pedestal trabecular node;
  determining angles between the bone trabeculae forming the pedestal trabecular nodes successively to obtain the angle data of each pedestal trabecular node.

In this embodiment, the performing feature analysis on the skeletal mechanical model subjected to obtain skeletal strength data, further includes:
  performing a finite element simulation on the angles between the trabecular bone nodes of the pedestal trabecular nodes to obtain the maximum stress of each angle type.

In this embodiment, the extracting at least one type of trabecular nodes as the pedestal trabecular nodes specifically includes: extracting a type of trabecular nodes with the largest quantity from various types of trabecular nodes as the pedestal trabecular nodes. Usually, the type of trabecular node with the largest quantity among the trabecular nodes is a trifurcated node, so the pedestal trabecular nodes are selected as trifurcated nodes. Of course, the pedestal trabecular nodes can also be selected to include multiple types of trabecular nodes.

Figure 5:
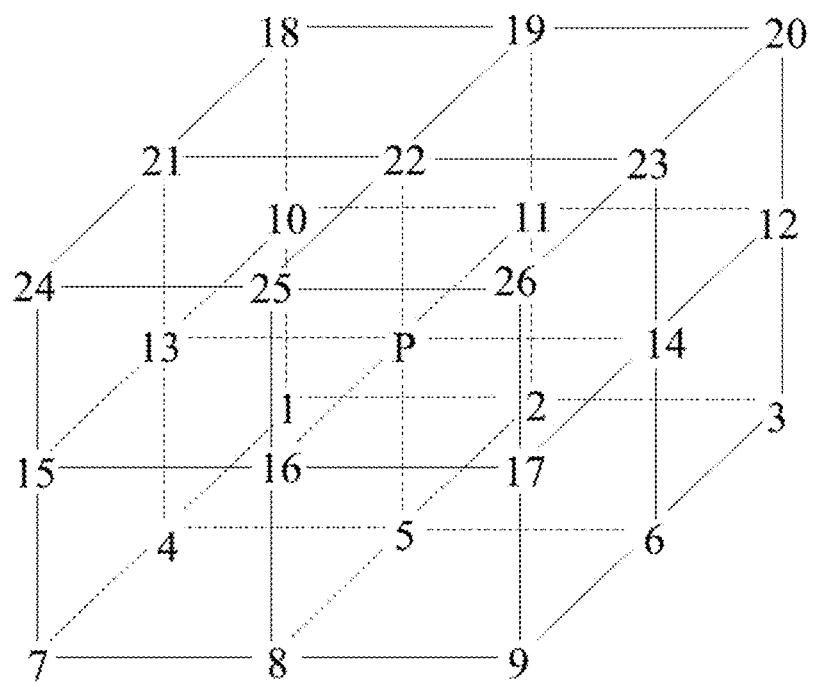
FIG. 5 is a schematic structural diagram of the three-dimensional voxel model described in Embodiment 1 of the present disclosure.

Referring to FIG. 4, the determining the quantity of trabeculae forming each trabecular node in the skeletal mechanical model described in this embodiment specifically includes:
  marking each pixel of the skeleton mechanical model according to the order of length*width*height l*m*n, and the range of the mark value is 0 to l*m*n−1;
  extracting pixels whose dark-and-bright indication values meet the preset skeleton threshold in the image of the skeleton mechanical model and marking the pixels as skeleton points;
  traversing the skeleton points of the skeleton mechanical model with a three-dimensional voxel model, extracting pixel points with more than three skeleton points at neighboring point positions, and marking the pixel points as candidate nodes; here, FIG. 5 illustrates a structure of the three-dimensional voxel model.
  pushing the coordinates of the candidate nodes into a stack as seed points for region growth, and setting the tag values of the candidate nodes as the tag values of the candidate nodes;
  performing the neighborhood search on the candidate nodes in the stack successively to determine whether the tag value of the candidate nodes is modified, and if not, popping the candidate nodes out of the stack until the distance between a spread candidate node and the first candidate node is greater than a preset search radius or there is no candidate node that can continue to spread;
  removing a candidate node whose distance from the candidate nodes in the stack is less than the preset minimum distance threshold, counting the quantity and coordinates of the remaining candidate nodes, and determining the quantity of trabecular bone forming the trabecular node according to the quantity of the remaining candidate nodes.

The image of the skeleton mechanical model is a binary image. The trabecular bone is represented by 1, and the non-trabecular bone position is represented by 0.

In this embodiment, the performing feature analysis on the skeleton mechanical model to obtain the skeleton strength data, includes, applying the following calculation formula of the first bone strength value to obtain the skeleton strength data:

$$E_1 = e\sigma_{yield} + fK + gM,$$

here, $E_1$ is the first bone strength value, e, f, and g are coefficients, $\sigma_{yield}$ is the maximum stress of the pedestal trabecular nodes, K is the weight of the proportion of discriminant trabecular nodes, and M is the weight of the proportions of the various angle modes in the pedestal trabecular nodes.

This embodiment further includes applying a machine learning method to train the first bone strength calculation formula.

In this embodiment, when applying a machine learning method to train the first bone strength value calculation formula, the method for obtaining training samples includes:
  performing an image scanning on the training bone segment, and performing geometric feature calculation and the finite element analysis on a training bone image obtained after scanning, conducting mechanical experiments on the training bone segment;
  obtaining the first bone strength marker value according to the calculation results of geometric features, the results of finite element analysis and the results of mechanical experiments;
  using the training bone segment and the first bone strength marker value of the training bone segment as the training samples.

Figure 6:
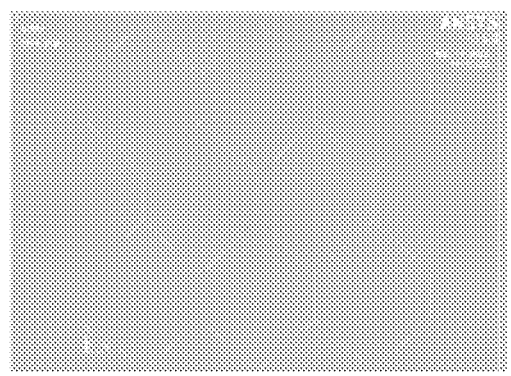
FIG. 6 is a schematic structural diagram of the first model described in Embodiment 1 of the present disclosure.
Figure 7:
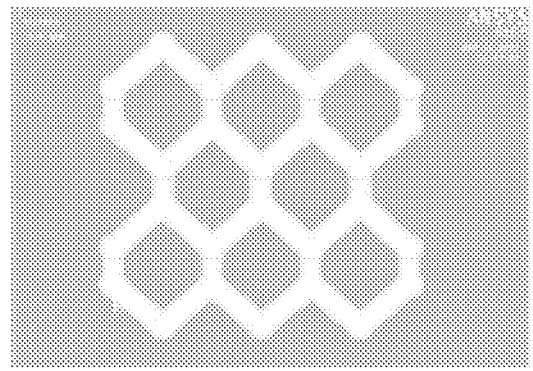
FIG. 7 is a schematic structural diagram of the second model described in Embodiment 1 of the present disclosure.

Referring to FIG. 6 and FIG. 7, the finite element analysis described in this embodiment is to classify the trifurcated nodes with different angle ranges according to the type of angle to obtain several types of trifurcated nodes with different angle ranges; using CATIA modeling software and ABAQUS mechanical analysis software to establish a network structure composed of hexagonal phases to form the first model in which one node connects three rods in space (as shown in FIG. 6), and add the cross-sectional area to the rods in the software, connect the rods with balls to form the second model representing the solid structure (as shown in FIG. 7).

The unit cells were taken for finite element analysis. The different types of unit cells have the same density (that is, the quantity of different types of trifurcated nodes in the unit space remains the same; the unit cell density refers to the ratio of the mass of the entity formed by the connection of "rods" and "balls" to the volume of space), and the boundary condition is applied, the same stress of 0.25 Mpa is applied to the upper side.

Nodes of different angle types have different strength values, for example:

Type 1: a trifurcated node with angles α=120°, β=120°, γ=120° between the three trabeculae, the stress at the maximum stress is 3.47 MPa;

Type 2: a trifurcated node with angles α=180°, β=120°, γ=90° between the three trabeculae, the stress at the maximum stress is 6.13 MPa.

When determining the bone strength based on the above data, the method can be referred to the following. The greater the stress at the maximum stress is, the more concentrated the stress is here, it is not easy to disperse the force, and it is easier to break. Of course, the method for evaluating bone strength is only based on the theory, but not limit the method for evaluating bone strength. As for how to apply the data obtained through the above methods, those skilled in the art can choose according to actual needs, and will not go into details here.

The nodes of different angle types have different mechanical properties. Through categorization, the nodes of different angle types are simulated by finite element, and the maximum stress of each type can be obtained, which forms the evaluation parameters for the description of trifurcated nodes. Similarly, quad nodes and pentagonal nodes also have different angle composition types and have different mechanical properties. The maximum stress of each type of trabecular nodes can be obtained through the above-mentioned finite element simulation method as evaluation data.

Embodiment 2

Figure 8:
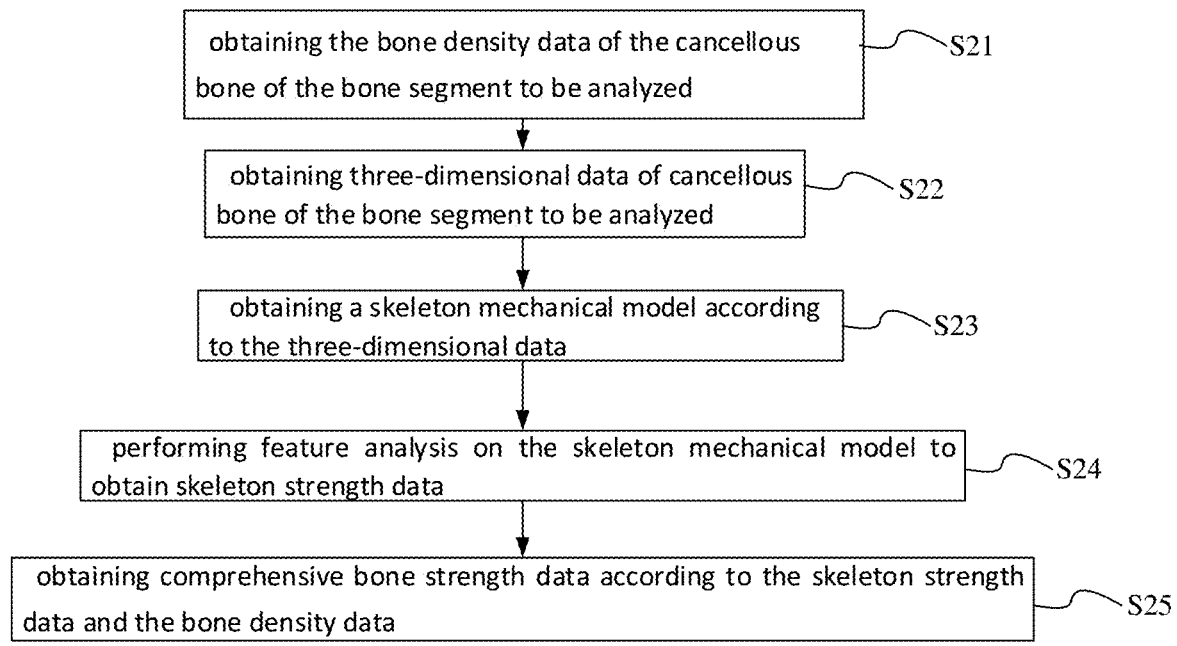
FIG. 8 is a flow chart of the bone strength assessment method described in Embodiment 2 of the present disclosure.

Referring to FIG. 8, some embodiments further provide a calculation method for a bone strength simulation, which includes:

obtaining the bone density data of the cancellous bone of the bone segment to be analyzed;

obtaining comprehensive bone strength data according to the skeleton strength data and the bone density data.

At this time, the calculation method for bone strength simulation specifically includes the following steps:

S21: obtaining the bone density data of the cancellous bone of the bone segment to be analyzed;

S22: obtaining three-dimensional data of cancellous bone of the bone segment to be analyzed;

S23: obtaining a skeleton mechanical model according to the three-dimensional data;

S24: performing feature analysis on the skeleton mechanical model to obtain skeleton strength data;

S25: obtaining comprehensive bone strength data according to the skeleton strength data and the bone density data.

In this embodiment, the method for obtaining the skeleton strength data may refer to the method shown in Embodiment 1, and the specific process will not be repeated here.

The bone strength simulation calculation method provided by the present disclosure further includes: obtaining the bone density data of the cancellous bone of the bone segment to be analyzed; obtaining the comprehensive bone strength data according to the skeleton strength data and the bone density data. Combining strength data with bone density data, comprehensively utilizing the internal features of each bone that affects bone strength to calculate comprehensive bone strength data, making the evaluation of bone strength more objective and comprehensive, and effectively improving the accuracy and credibility of bone strength evaluation.

In this embodiment, the obtaining comprehensive bone strength data according to the skeleton strength data and the bone density data, includes: applying the following formula for calculating comprehensive bone strength to obtain the comprehensive bone strength data:

$$E = aT + b\sigma_{yield} + cK + dM;$$

here, E is the comprehensive bone strength value, a, b, c, d are coefficients, T is bone density data, $\sigma_{yield}$ is the maximum stress of the pedestal trabecular nodes, and K is the weight of the proportion of discriminant trabecular nodes, M is the weight of the proportions of the various angle modes in the pedestal trabecular nodes.

This embodiment further includes applying a machine learning method to train the formula for calculating the comprehensive bone strength value.

In this embodiment, when applying the machine learning method to train the formula for calculating the comprehensive bone strength value, the method for obtaining training samples includes:

performing a bone density calculation and image scanning on the training bone segment, and performing a geometric feature calculation and finite element analysis on the training bone image obtained after scanning; conducting mechanical experiments on the training bone segment;

obtaining the comprehensive bone strength marker value according to a bone density calculation result, a geometric feature calculation result, a finite element analysis result and mechanical experiment results;

marking the training bone segment and the comprehensive bone strength marker value of the training bone segment training samples.

The present disclosure further provides a bone strength simulation computing device, which includes a processor and a memory. The computer instructions are stored in the memory, and the processor is configured to execute the computer instructions stored in the memory. When the computer instructions are executed by the processor, the device implements the steps of any one of the methods described above.

The present disclosure further provides a computer storage medium, on which a computer program is stored, and when the computer program is executed by a processor, any one of the methods described above are realized.

Finally, it should be noted that the above embodiments are only used to illustrate the technical solutions of the present disclosure, rather than limiting them. Although the present disclosure has been described in detail with reference to the foregoing embodiments, those of ordinary skill in the art should understand that it is still possible to modify the technical solutions described in the foregoing embodiments, or perform equivalent replacements for some or all of the technical features, and these modifications or replacements do not make the essence of the corresponding technical solutions deviate from the scope of technical solutions of the various embodiments of the present disclosure.

What is claimed is:

1. A bone strength simulation calculation method, comprising:
   obtaining three-dimensional data of a cancellous bone of a bone segment to be analyzed;
   obtaining a skeleton mechanical model according to the three-dimensional data;
   performing a feature analysis on the skeleton mechanical model to obtain skeleton strength data;
   wherein trabeculae in the cancellous bone are interwoven with each other, and joints of three or more trabeculae are trabecular nodes;
   the skeleton strength data comprises a quantity of the trabecular nodes, and data of angle between trabecular bones of the trabecular nodes;
   wherein the performing a feature analysis on the skeleton mechanical model to obtain skeleton strength data, comprises:
   determining a quantity of bone trabeculae constituting each trabecular node in the skeleton mechanical model to obtain a type of each trabecular node; extracting a quantity of discriminant trabecular nodes in various types of trabecular nodes; extracting at least one type of trabecular node as a pedestal trabecular node; determining angles between each bone trabeculae constituting the pedestal trabecular node successively to obtain data of angles between each pedestal trabecular node;
   performing a finite element simulation on the angles between the trabecular bones of the pedestal trabecular nodes to obtain a maximum stress of each angle type.

2. The bone strength simulation calculation method according to claim 1, wherein the discriminative trabecular nodes comprise trifurcated nodes, quad nodes, and pentagonal nodes.

3. The bone strength simulation calculation method according to claim 1, wherein the extracting at least one type of trabecular node as a pedestal trabecular node, comprises:
   extracting a type of trabecular node with a largest quantity from various types of trabecular nodes as the pedestal trabecular node.

4. The bone strength simulation calculation method according to claim 3, wherein the pedestal trabecular node comprises trifurcated nodes.

5. The bone strength simulation calculation method according to claim 1, wherein the determining a quantity of bone trabeculae constituting each trabecular node in the skeleton mechanical model, comprises:
   marking each pixel of the skeleton mechanical model according to an order of length*width*height l*m*n, wherein a range of mark value is 0 to l*m*n−1;
   extracting pixels whose dark-and-bright indication values meet a preset skeleton threshold in an image of the skeleton mechanical model, marking the pixels as skeleton points;
   traversing the skeleton points of the skeleton mechanical model with a three-dimensional voxel model, extracting with more than three skeleton points at neighboring point positions, and marking the pixel points as candidate nodes;
   pushing coordinates of the candidate nodes into a stack as a seed point for region growth, and setting a tag value of the candidate nodes as a tag value of the candidate nodes;
   performing a neighborhood search on the candidate nodes in the stack successively to determine whether the tag value of the candidate nodes is modified, and if not, popping the candidate nodes out of the stack until a distance between a spread candidate node and a first candidate node is greater than a preset search radius or there is no such spread candidate node;
   removing a candidate node whose distance from the candidate nodes in the stack is less than a preset minimum distance threshold, counting a quantity and coordinates of remaining candidate nodes, and determining a quantity of trabecular bone forming the trabecular node according to the quantity of the remaining candidate nodes.

6. The bone strength simulation calculation method according to claim 5, further comprising:
   obtaining bone density data of the cancellous bone of the bone segment to be analyzed;
   obtaining comprehensive bone strength data according to the skeleton strength data and the bone density data.

7. A bone strength simulation calculation device, comprising a processor and a memory, wherein the memory is configured to store computer instructions, and the processor is configured to execute the computer instructions stored in the memory, in response to the computer instructions are executed by the processor, the device implements the method according to claim 1.

8. A computer storage medium, storing a computer program, wherein in response to the computer program being executed by a processor, the method according to claim 1 is implemented.

9. The bone strength simulation calculation method according to claim 1, wherein the obtaining three-dimensional data of a cancellous bone of the bone segment to be analyzed, comprises:
   obtaining the three-dimensional data of the cancellous bone of the bone segment to be analyzed by using a Quantitative Computed Tomography, QCT measurement method.

10. The bone strength simulation calculation method according to claim 1, wherein the obtaining a skeleton mechanical model according to the three-dimensional data, comprises:
    performing a three-dimensional reconstruction according to the three-dimensional data to obtain a spatial structure of a trabecular bone;
    skeletonizing obtained spatial structure of the trabecular bone to obtain a mechanical model of the trabecular bone, wherein the mechanical model of the trabecular bone is the skeleton mechanical model.

* * * * *